United States Patent [19]

Stordahl

[11] Patent Number: 5,018,970
[45] Date of Patent: May 28, 1991

[54] IMPLANT TEETH—PERMANENT BASES WITH REPLACEABLE CAPS

[76] Inventor: Finn R. Stordahl, 8914 N. Sun Lakes Blvd., Sun Lakes, Ariz. 85248

[21] Appl. No.: 508,681

[22] Filed: May 5, 1989

Related U.S. Application Data

[63] Continuation-in-part of Ser. No. 134,255, Dec. 17, 1987.

[51] Int. Cl.⁵ .................................................. A61C 3/00
[52] U.S. Cl. ........................................ 433/75; 433/76; 433/116; 433/144; 433/173
[58] Field of Search ............... 433/173, 174, 175, 176, 433/75, 76, 116, 144

[56] References Cited

U.S. PATENT DOCUMENTS

| | | | |
|---|---|---|---|
| 2,224,264 | 12/1940 | Jeanneret | 433/75 |
| 2,258,207 | 10/1941 | Irwin | 433/173 |
| 2,347,567 | 4/1944 | Kresse | 433/174 |
| 3,011,259 | 12/1961 | Baum | 433/75 |
| 3,108,376 | 10/1963 | Weinger | 433/144 |
| 3,738,008 | 6/1973 | Edelman | 433/176 |
| 4,177,562 | 12/1979 | Miller et al. | 433/174 |
| 4,220,712 | 9/1980 | Staffolani | 433/173 |
| 4,253,833 | 3/1981 | Edelman | 433/173 |
| 4,941,826 | 7/1990 | Loran et al. | 433/76 |

Primary Examiner—John J. Wilson

[57] ABSTRACT

The present invention relates to dental endosteal implants with devices to aid in the placement of the implant, and procedures for placing the implant.

6 Claims, 3 Drawing Sheets

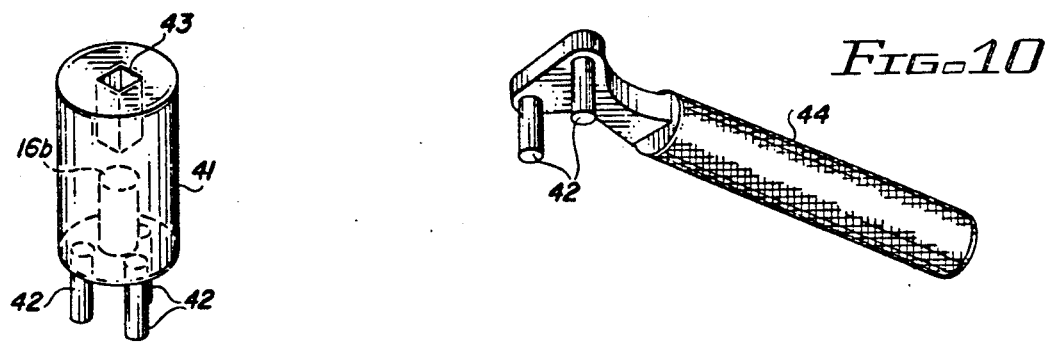
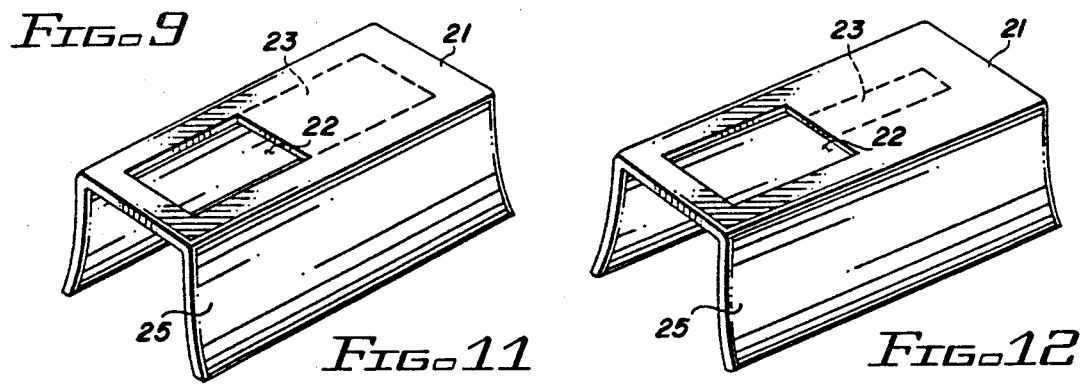
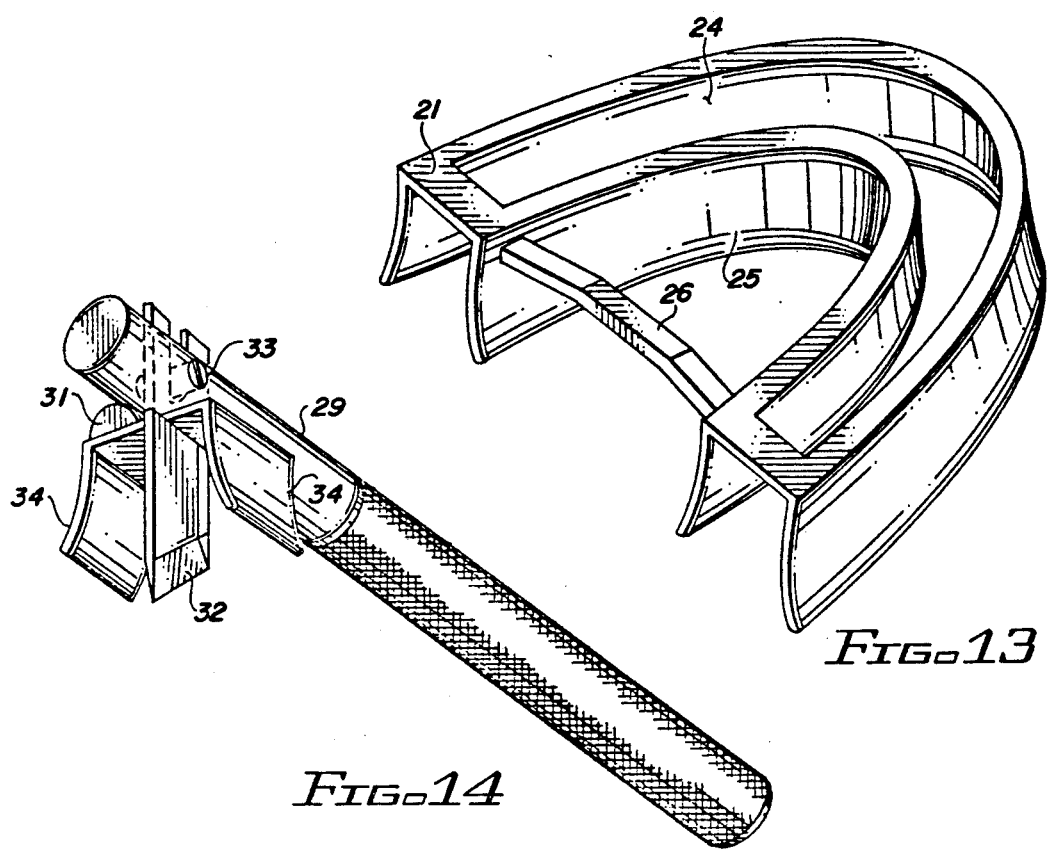

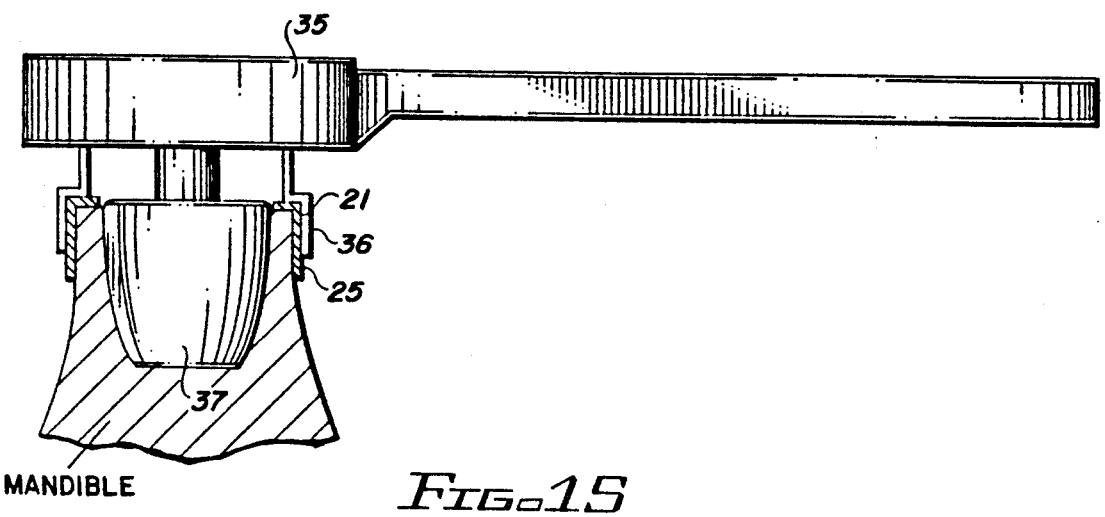
MANDIBLE  FIG. 15
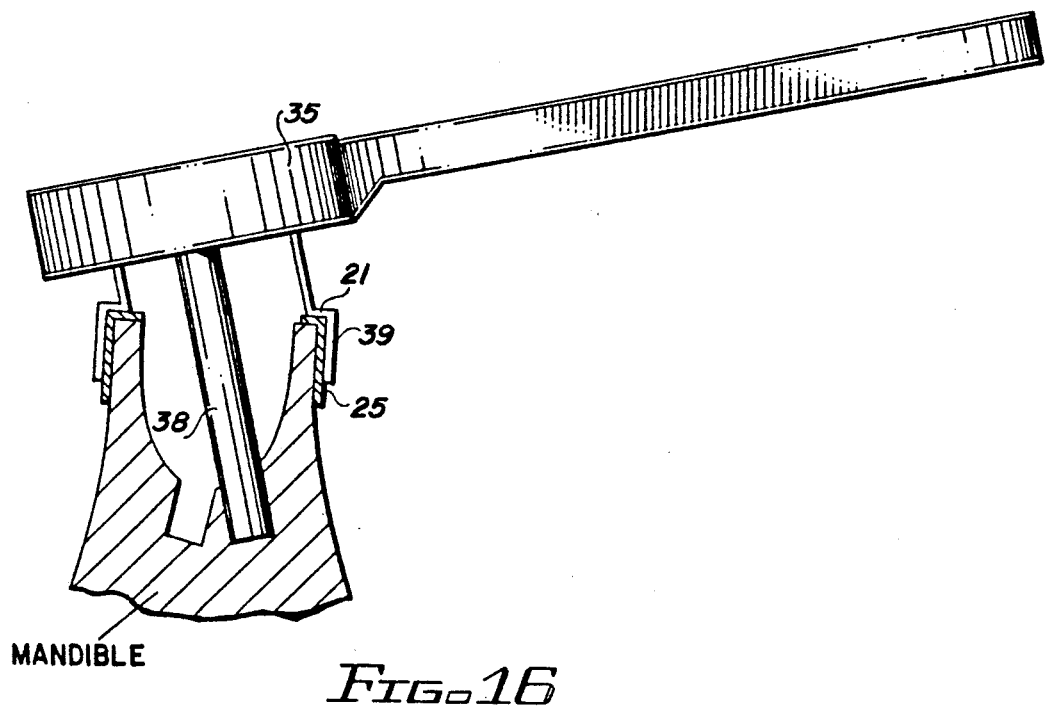
MANDIBLE  FIG. 16

IMPLANT TEETH—PERMANENT BASES WITH REPLACEABLE CAPS

This application is a continuation-in-part of Ser. No. 07/134,255 filed Dec. 17, 1987.

Previously, as described in several patents, particularly U.S. Pat. Nos. 3,738,008 and 4,220,712, a hole was drilled into the jaw bone and the implant was driven into this small area; and with extreme force, tips were radically turned outward and upward. Without a torque gauge, the possibility of severely damaging the jaw bone is inherent in this procedure.

It is the object of this invention to provide a new and unique method for an implant producing a more stabilized footing better able to withstand the pressures of masticating. Instead of a small hole, the present implant lays smoothly (and is supported by displacement, as is a large vessel by water) in a section of the jaw bone; thus eliminating the possibility of jaw bone damage, as aforementioned in previous patents.

This invention includes an implant composed of several parts including a (permanent) base, a (replaceable) stem and a (replaceable) cap. The base has at its lower end two flanges, with the option of at least one of the flanges being moveable. In the upper end of the base there is a threaded hole, which is mated to the threaded bottom of the stem, for flush installation there-in-to. It is to this installed stem to which the (replaceable) cap adheres.

BRIEF DESCRIPTION OF THE DRAWINGS

FIG. 9 is a top perspective view showing the socket used to install or remove replaceable stem of FIG. 8.

FIG. 10 is a top view of a wrench to install or remove the replaceable stem of FIG. 8.

FIGS. 11-12-13 are scalpel and router jigs, shown in perspective, used for cutting the gum and routing the jaw bone in single, adjoining and full denture replacement procedures according to the present invention.

FIG. 14 is a perspective view of a gum cutting scalpel which can be used in conjunction whith the jigs of FIGS. 11-12-13.

FIGS. 15 AND 16 are side views of the router, guide, and bit utilized to drill the central implant dado groove and the angled dado grooves to accomodate the base flanges.

DETAILED DESCRIPTION OF THE INVENTION

Figure 1:
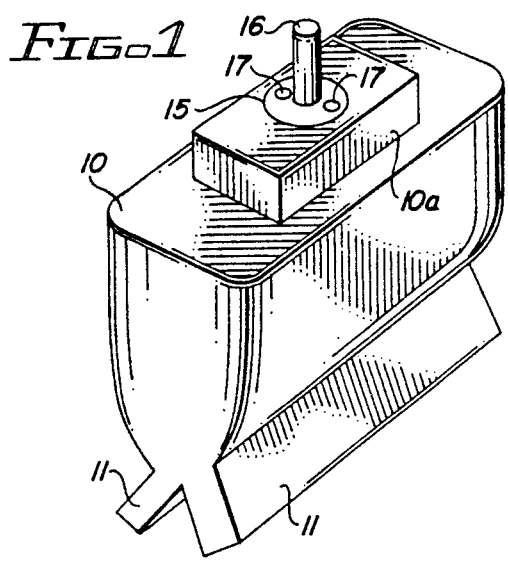
FIG. 1 is a partial front and top view to give an overall view of the implant base.

FIG. 1 is shown to illustrate an over-all look of the base.

Figure 2:
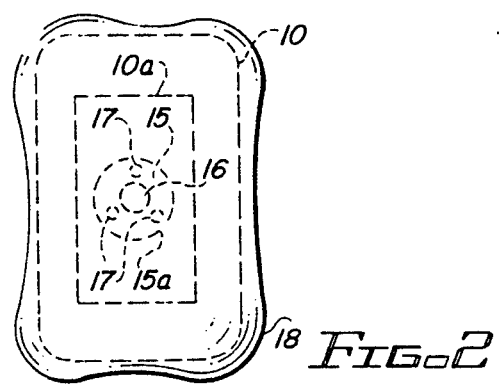
FIG. 2 is a top view of a cap which fits upon the base and stem of FIGS. 1-4-5-6-7.
Figure 3:
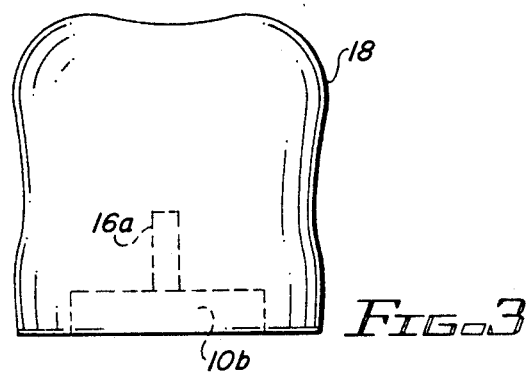
FIG. 3 is a side view of a cap which fits upon the base and stem of FIGS. 1-4-5-6-7.

FIGS. 2 and 3 show the cap 18 used in the replacement of a molar. Within the cap 18 are indentations 10b and 16a of sizes to closely match the straight sided rectangular ridge 10a and post 16 over which it will be placed. Other caps 18 which are to replace other teeth will have a similar internal structure. The basically rectangular shaped 18 is sized so that the length is equal to the base 19, and is sized as in FIG. 2 so that there is enough width to overlay the edges of the primary dado cut as in FIG. 15, for added strength during the masticating process. The extra cap width will permit the gum to return to its normal position, on a parallel with the jaw bone, and above the bottom of cap 18, for both hygenic benefit and cosmetic appearance.

Figure 4:
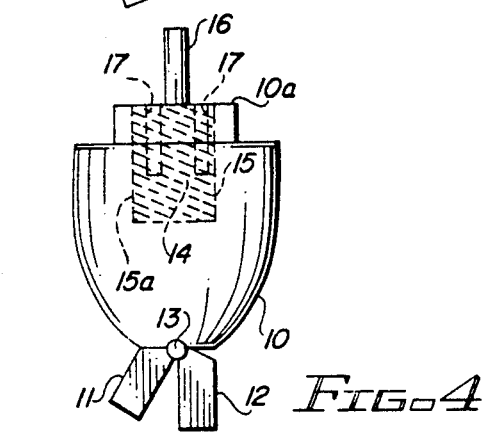
FIG. 4 is a front partial cutaway view of a base and stem combination of a dental implant according to the present invention.
Figure 5:
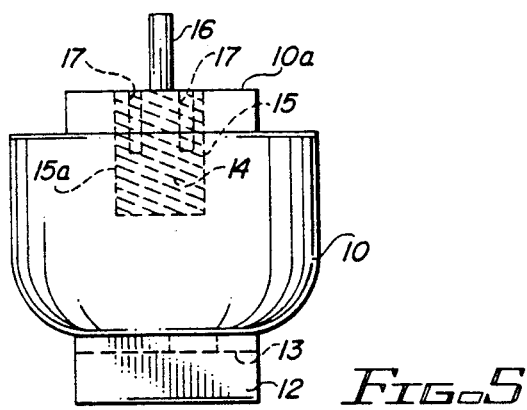
FIG. 5 is a side view base and stem combination of FIG. 3.

FIGS. 4 and 5—The first embodiment of the invention, shown in FIGS. 1 and 4-5, is a single base structure 10, which will utilize its shape to stabilize the implant. The lower end of the base 10, which is implanted into the jaw bone, has in the preferred embodiment, at least one stationary flange 11 and the option of at least one moveable flange 12. The moveable flange 12 may be attached to the bottom of the base 10 by a hinge arrangement 13 or other suitable structure which allows it to be rotated from its closed position for insertion (the dotted position in FIG. 4) to the open implanted position as shown in solid lines.

In this invention, an immediate tooth replacement can take effect, where both flanges 11 are fixed on the base and the cap 18 completely installed on the base 10. However, it is not necessary that flanges normally be fixed, as one, or both may be designed to rotate. The top of the base 10 has a threaded hole 14 therein to accept a stem 15, the stem having a precisely matched thread pattern 14. The base 10 is composed of biocompatable materials currently utilized by the trade for similar dental applications.

Figure 7:
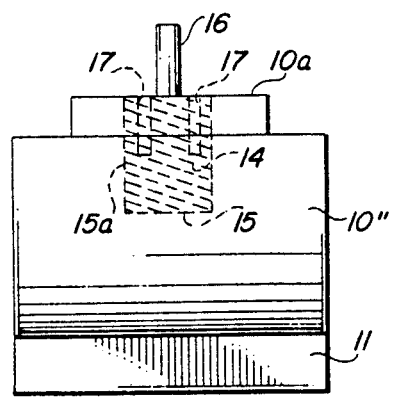
FIG. 7 is a side view of a base and stem utilized between end base structures in a multiple base application.
Figure 6:
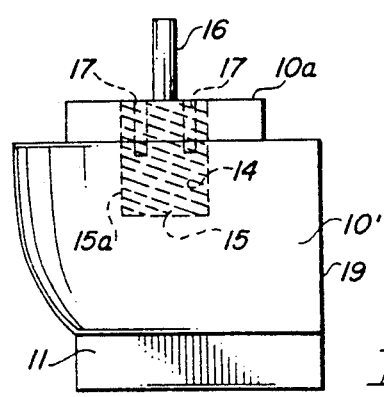
FIG. 6 is a side view of an end base and stem structure useful in a multiple base application.

FIGS. 6 and 7 show a second embodiment of the base 10 wherein several adjacent implants are to be placed into the bone. The base 10' of FIG. 6, used on the end(s) in a multiple base application, and has an adjacent edge 19 which conforms to a mating edge 20 of a center base 10". While it is desired that the adjacent bases be in contact with each other, to give added structural rigidity they may be spaced from each other or, in the alternative, made to interlock with each other. A similar but mirror image to base 10' would be used on the other end of the multiple base, or base 10' could be reversed so that the adjacent edges 19 could butt upon each other for a dual implant. The base structures 10' and 10" utilize the same design stem 15 and cap 18 as the earlier described embodiment.

Figure 8:
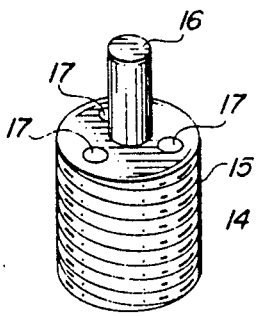
FIG. 8 is a perspective view of the repaceable stem of FIGS. 1-4-5-6-7.

FIG. 8 shows the replaceable stem 15, which is placed in the base 10 as shown in FIGS. 1-4-5-6-7. The stem is threaded (14) so that it can be removed from the base 10 if needed. At the top of the stem 15 is a post 16, fluted so that a cap 18 can easily be placed thereon and readily adhered thereto using quality glues or epoxy resins. The fluting helps to lock the cap 18 to the post 16 once the adhesive takes effect. It is contemplated that other mechanical means can be used to secure the cap 18 to the post 16. The stem 15 also has at least two holes 17 located in the top thereof for use in tightening the stem 15 into, or removing the stem 15 from the base 10.

FIGS. 9—the socket 41 is for use to tightly insert the replaceable stem 15 into the base 10. The socket 41, preferably composed of a high strength metal, has pegs 42 on the bottom thereof that match the tightening holes 17 in the stem 15. In the top of socket 41 is a square shaped rachet hole 43 into which a ratchet wrench (not shown) is placed. The socket 41 can also be used to remove the stem 15 from the base 10 should replacement be necessary.

FIG. 10—another means for installing or removing the replaceable stem 15 is wrench 44, which has similarly placed pegs 42, designed to match the stem tightening holes 17.

FIGS. 11-12-13 show jigs which are used as a guide for a gum cutting scalpel and a mandible/maxilla router. Depending on the number and size of teeth to be implanted, several jigs 21 may be required. For example, FIG. 4 shows a jig 21 for a single large tooth, such as a molar. If two adjacent teeth of the same size are to be implanted, the area 23 enclosed by dotted lines would be opened. A reduced adjacent cutout 24 would be used where two teeth of dissimilar size are to be implanted, such as a canine tooth next to a molar. In use, the jig 21 is placed over the area of the gum to be operated upon, with a skirt 25 placed on both sides of the aveolar ridge. While the jig 21 shown is linear in structure it is contemplated that the jig could also be curved to better fit the natural curve of the gum line. This is shown in FIG. 13 which shows a jig 21 utilized for a full denture replacement or when several implants are to be made in the same jaw, but natural teeth are to be left undisturbed.

FIG. 14 shows the gum cutting scalpel 29 utilized in conjunction with a jig 21 in the implant procedure, consisting of a handle 30 with a scalpel guide 31 and cutting blade 32 mounted on the end thereof by threaded connectors 33. To cut the center line of the gum the scalpel guide rests on the upper surface of the jig 21 with the wing 34 riding along the jig skirt 25. With the guide and wing, 31 and 34 removed, the blade can be used to peal away the gum from the maxilla/mandible area.

FIGS. 15 and 16 depict the utilization of router 35 hollowing out the jaw bone to receive the implant. The router can be either electrically or fluid driven, as is common in the dental or orthopedic arts for forming holes in bone. The under surface of the router is modified to receive a jig riding guide 36. In use, the guide 36 rests on top of a jig 21. A bit 37 is sized and attached to the router 35 in such a manner that the router 35, guide 36 and jig 21 interact to closely control the depth of the cut into the mandible and/or maxilla at the various locations of molars, canines and incisors. While different shaped router bits may be utilized, the router bit 37 shown in FIG. 15 is preferably shaped to produce a dado cut which results in enabling a precise implant shape to absorb the preferred balanced over-all pressure more thoroughly between the implant base 19 and the jaw bone during mastication.

FIG. 16 shows a router bit 38 for forming straight dado cuts 49, into which the flanges 11 and/or 12 are placed. The precise angle at which the flange depressions are routed is controlled by replacing jig over-riding guide 36 by a guide 39 which provides the necessary offset to create the dado cut 40. To produce the precise opposite angle cut 40, the guide 39 is reversed.

What is claimed is:

1. A dental jig for precisely holding and guiding a dental cutting tool for cutting the gum and bone for implanting a dental implant, said jig comprising a central portion and two skirt portions extending from said central portion, said central portion having at least one opening through which a cutting element of said cutting tool passes, said jig further comprising a tool guide, said tool guide having means for connecting said guide to a dental cutting tool and further having two wing portions, said two skirt portions and said two wing portions being removably engaged to provide guiding surfaces, whereby in use the jig is placed over the alveolar ridge with the two skirts covering the gum and a dental cutting tool having the tool guide attached thereto is inserted through said opening with the wing portions engaging the skirt portion to guide said tool while cutting.

2. A jig as claimed in claim 1 wherein the jig and opening are sized to extend over several existing teeth for cutting in several areas at the same time.

3. A jig as claimed in claim 1 and further including in combination therewith a scalpel for cutting the gum, said scalpel having a handle and a cutting blade, said tool guide being attached to said scalpel so that a wing extends along opposite sides of said blade, whereby when the blade is placed through said opening, the wings engage the skirts and guide the blade to precisely cut along the center of the aveolar gum.

4. A jig as claimed in claim 1 and further including therewith a router for drilling openings in the jaw bone, said router having a handle and a router bit extending therefrom, said tool guide being attached to said router so that a wing extends along opposite sides of said router bit, whereby when the blade is placed through said opening, the wings engage the skirts and guide the bit to precisely cut into the jaw bone.

5. A jig and router as claimed in claim 4 wherein, said wings extend straight down, whereby a straight hole will be drilled in the jaw bone.

6. A jig and router as claimed in claim 4 wherein, the wings extend down at an angle, whereby an angled hole is cut into the jaw bone and whereby, by reversing the wings the drill will cut two precisely angled holes at apposite angles.

* * * * *